United States Patent
Stiger et al.

(10) Patent No.: US 6,547,813 B2
(45) Date of Patent: Apr. 15, 2003

(54) STENT DELIVERY CATHETER WITH FOLDED SLEEVE AND METHOD OF MAKING SAME

(75) Inventors: Mark L. Stiger, Santa Rosa, CA (US); Michael A. Mohn, Santa Rosa, CA (US)

(73) Assignee: Medtronic Ave, Inc., Santa Rosa, CA (US)

( * ) Notice: Subject to any disclaimer, the term of this patent is extended or adjusted under 35 U.S.C. 154(b) by 81 days.

(21) Appl. No.: 09/815,615

(22) Filed: Mar. 23, 2001

(65) Prior Publication Data

US 2002/0138127 A1 Sep. 26, 2002

(Under 37 CFR 1.47)

(51) Int. Cl.⁷ .................................................. A61F 2/06
(52) U.S. Cl. ................................................... 623/1.11
(58) Field of Search ............................ 623/1.11, 1.12, 623/1.23; 606/108, 191–195, 198; 604/96.01, 103.06, 103.07, 103.08, 915, 916, 101.01, 101.05

(56) References Cited

U.S. PATENT DOCUMENTS

| | | | |
|---|---|---|---|
| 4,732,152 A | * 3/1988 | Wallsten et al. ............ 623/1.11 |
| 4,950,227 A | 8/1990 | Savin et al. | |
| 5,108,416 A | 4/1992 | Ryan et al. | |
| 5,116,318 A | 5/1992 | Hillstead | |
| 5,254,091 A | * 10/1993 | Aliahmad et al. ........... 606/194 |
| 5,344,426 A | * 9/1994 | Lau et al. ................... 623/1.11 |
| 5,403,341 A | 4/1995 | Solar | |
| 5,409,495 A | 4/1995 | Osborn | |
| 5,425,710 A | 6/1995 | Khair et al. | |
| 5,445,646 A | 8/1995 | Euteneuer et al. | |
| 5,549,635 A | 8/1996 | Solar | |
| 5,571,135 A | 11/1996 | Fraser et al. | |
| 5,643,278 A | 7/1997 | Wijay | |
| 5,662,703 A | 9/1997 | Yurek et al. | |
| 5,741,326 A | 4/1998 | Solovay | |
| 5,766,201 A | 6/1998 | Ravenscroft et al. | |
| 5,807,327 A | * 9/1998 | Green et al. ................ 623/1.11 |
| 5,807,398 A | 9/1998 | Shaknovich | |
| 5,810,871 A | 9/1998 | Tuckey et al. | |
| 5,817,100 A | 10/1998 | Igaki | |
| 5,843,027 A | 12/1998 | Stone et al. | |
| 5,935,135 A | 8/1999 | Bramfitt et al. | |
| 5,944,726 A | 8/1999 | Blaeser et al. | |
| 5,951,569 A | 9/1999 | Tuckey et al. | |
| 5,964,730 A | 10/1999 | Williams et al. | |
| 5,968,069 A | * 10/1999 | Dusbabek et al. ........... 606/194 |
| 5,976,155 A | 11/1999 | Foreman et al. | |
| 6,048,356 A | 4/2000 | Ravenscroft et al. | |
| 6,056,906 A | 5/2000 | Werneth et al. | |
| 6,063,112 A | 5/2000 | Sgro | |
| 6,110,180 A | 8/2000 | Foreman et al. | |
| 6,168,617 B1 | * 1/2001 | Blaeser et al. ............. 623/1.11 |
| 6,174,316 B1 | 1/2001 | Tuckey et al. | |
| 6,280,412 B1 | 8/2001 | Pederson, Jr. et al. | |
| 6,391,032 B2 | * 5/2002 | Blaeser et al. ............. 606/108 |
| 6,432,080 B2 | * 8/2002 | Pederson et al. ........ 604/103.07 |

FOREIGN PATENT DOCUMENTS

EP      0 553 960 A1     8/1993

* cited by examiner

*Primary Examiner*—Michael J. Milano
*Assistant Examiner*—Jessica R. Baxter

(57) ABSTRACT

A stent delivery catheter and method for making the same includes a tubular balloon, an elastic sleeve, and a stent. The balloon is mounted around a catheter shaft, and the stent is crimped onto the balloon. The elastic sleeve is positioned between the balloon and the stent, the sleeve extending beyond the ends of the stent where the ends of the sleeve are fixed to the catheter shaft. Sleeve material is gathered and folded over the ends of the stent to retain the stent snugly against the balloon during delivery.

15 Claims, 4 Drawing Sheets

STENT DELIVERY CATHETER WITH FOLDED SLEEVE AND METHOD OF MAKING SAME

FIELD OF THE INVENTION

The present invention relates generally to medical catheters. More specifically, the present invention relates to catheters which can be used to deliver a stent to a deployment site in the cardiovascular system of a patient.

BACKGROUND OF THE INVENTION

Stents are devices deployed in the cardiovascular system of a patient to maintain the patency of a vessel at the site of a lesion. Typically, this requires advancement of the stent through the cardiovascular system and then deployment of the stent at a stenosis site in the vessel where the lesion has developed. A balloon-expandable stent is delivered by securing it onto a balloon of a delivery catheter which then may be advanced through the vascular system to the stenosis site. Once at the stenosis site, the balloon is inflated to deploy the stent.

Significantly, the delivery catheter must bend in different directions as it follows one of the tortuous routes through the vascular system to the stenosis site. As the catheter bends, the attached stent will also bend, and the ends of the stent may deform and flare outwardly from the balloon, thereby increasing the profile of the stent. With such an increased profile the stent may not advance further through the cardiovascular system to cross the lesion site, or the stent may not be easily withdrawn from the body, if that is desired. It is preferred that the stent be retained snugly against the balloon until the stenosis site is reached. Once the stent is placed across the stenosis, the stent should quickly and easily separate from the catheter after the balloon inflates during the deployment of the stent.

Various devices have been proposed to retain the stent against the balloon in a delivery catheter. In several prior art devices, pairs of separate sleeves, caps or cuffs are mounted over the stent proximal and distal ends to prevent their premature expansion. In one of such devices, the cuffs are mounted on a stent-carrying, tubular cartridge which may be slid over the balloon of any suitable stent delivery catheter. In another prior art example, the ends of a balloon-mounted stent are overlaid by cuffs formed from excess material of the balloon.

In yet another prior art device, retention sleeves self-retract from their positions overlying the ends of the stent during inflation of a balloon. In this case, the sleeves are anchored to a catheter shaft, and they need to fold or accordion to reduce their overall length while sliding down the cones of the expanding balloon. For the devices mentioned above, the ends of the stent must slide out from under the end caps as the balloon expands the diameter of the stent.

In yet another device, a stent is mounted on a delivery balloon that has been wrapped with elastic material, and slidable caps cover the ends of the stent until the balloon is inflated. However, in all devices that utilize stent end caps, the stent may fail to completely exit from within a cap during deployment, possibly leaving the cap caught between the stent and the vessel wall after the balloon has been deflated. To avoid this problem, the end caps may be mounted with only a short overlap of the stent ends, which can lead to premature uncovering of the stent ends and concomitant loss of retention.

With the above in mind, it is an object of the present invention to provide a catheter for delivering a stent which retains the stent snugly against the catheter balloon during advancement into the vascular system.

SUMMARY OF THE INVENTION

In accordance with the present invention, a device for retaining a stent on the balloon of a delivery catheter includes a flexible, elastic sheath, or sleeve, that is positioned over the balloon on the delivery catheter. After the stent is crimped into place over the sleeve, circumferential folds of sleeve material are formed to lie over the ends of the stent and thereby hold the stent on the balloon until it is deployed. During deployment of the stent, the inflation of the balloon stretches the sleeve, essentially eliminating the folds and thus ensuring release of the stent from the catheter. The invention features a reliable mechanism to withdraw the retention folds from the ends of the stent during deployment, such that the folds of the present invention can cover wider margins at the ends of the stent than were previously advisable, thus providing more dependable retention of the stent on the catheter.

In a preferred method of making the present invention, a balloon delivery catheter is provided with its balloon uninflated and wrapped, or furled. While the balloon remains wrapped, the sleeve is positioned over the balloon, and the stent is crimped onto the balloon-sleeve combination. The ends of the sleeve are then bonded to the catheter adjacent the ends of the balloon. The sleeve material is gathered and formed into folds adjacent the ends of the stent.

Next, the proximal fold is pulled in the distal direction and folded over the proximal end of the stent, and the distal fold is pulled in a proximal direction and folded over the distal end of the stent. The folds are then heat set to hold their shape. Thus, the sleeve is formed with a distal fold and a proximal fold, both of which are used to help retain the stent in place around the balloon. The sleeve is preferably made of an elastomeric material such as a low durometer synthetic rubber.

The heat setting process is preferably provided using heat-shrink tubing to provide compression force during heating. In addition to setting the folds over the ends of the stent, the heat and compression can also be used to embed the folds into the stent to establish a firm grip on the stent. The heat setting process also reduces the profile of the catheter to facilitate insertion of the delivery catheter into the cardiovascular system of a patient.

In operation of the present invention, a delivery catheter with sleeve and stent are advanced into the cardiovascular system of a patient until the stent has been properly positioned within the stenosis for deployment. During this advancement, the ends of the stent are held in a restrained position against the deflated balloon by the proximal and distal folds in the sleeve. After the stent is properly positioned, the balloon is inflated to expand the sleeve and the stent. The expansion of the balloon causes the proximal and distal sleeve folds to unfold and smooth out, withdrawing the folds from over the ends of the stent. Subsequently, as the balloon is deflated for removal of the delivery catheter from the patient's cardiovascular system, the elastic sleeve contracts along with the balloon, thus assisting in the re-wrapping of the collapsing balloon. The result is an overall reduction in the profile of the sleeve and the deflated balloon. The delivery catheter, with its reduced deflated balloon profile, is withdrawn from the patient while the stent remains deployed in the patient's vessel

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
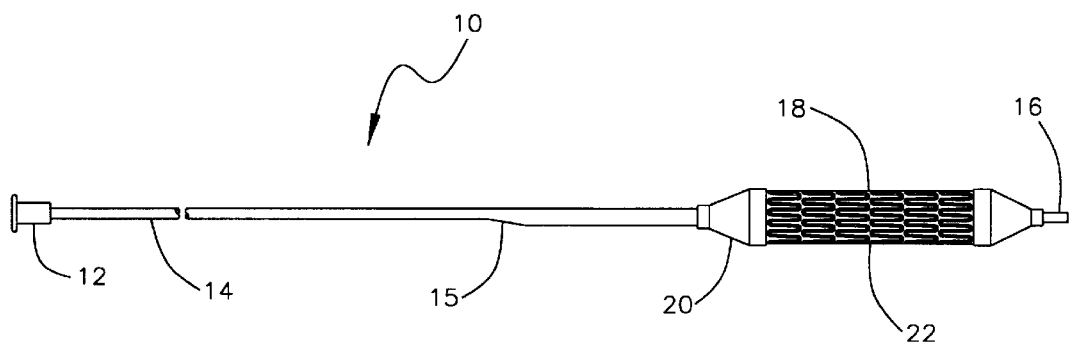
FIG. 1 is an illustration of a stent delivery catheter in accordance with the invention prior to expansion of the stent.
Figure 2:
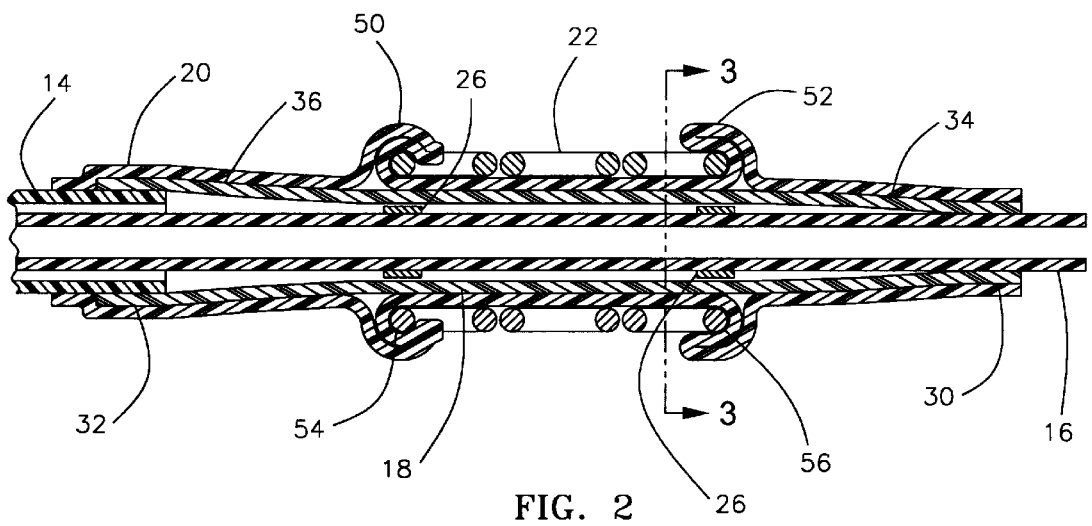
FIG. 2 is a longitudinal cross sectional view of the distal end of the invention prior to expansion of the stent.

Applicant's invention is advantageous with any expandable cylindrical stent, such as those stents designed for delivery by a tubular balloon. FIG. 1 shows stent delivery catheter 10 in accordance with the present invention. Catheter 10 includes luer fitting 12 which is attached in fluid communication with proximal shaft 14. Distal shaft 16 is preferably the inner tube of a coaxial catheter design, as depicted in FIG. 2, wherein distal shaft 16 extends through proximal shaft 14, creating an annular inflation lumen therebetween. In an alternative design, not shown, distal shaft 16 may be a single lumen extension of a multi lumen proximal shaft, the two shaft portions being joined adjacent or proximal to the balloon proximal neck 32. Either a multi lumen extrusion or a coaxial assembly may be used to construct either an over-the-wire type catheter or a rapid exchange type catheter. FIG. 1 shows a rapid exchange type catheter, in which proximal guidewire port 15 is located generally distally in shaft 14. The features of the invention may also be designed into a fixed-wire balloon catheter wherein distal shaft 16 would surround a guidewire that is integral to the catheter assembly. In all cases, distal shaft 16 extends distally of proximal shaft 14 to provide a lower profile in the distal region of the catheter. All of the shaft designs mentioned above are well known to artisans in the field of cardiovascular catheters.

Catheter 10 includes balloon 18, sleeve 20 which covers balloon 18, and stent 22 which is mounted over sleeve 20, as shown in FIG. 2. Balloon 18 has a generally cylindrical body 28 for receiving a stent, and distal and proximal cones 34, 36, which taper respectively to distal and proximal bands, or necks 30, 32 respectively. Balloon 18 is mounted adjacent the distal end of catheter 10, surrounding distal shaft 16. Balloon distal neck 30 is fixed to distal shaft 16, and balloon proximal neck 32 is fixed to, or alternatively may be an integral extension of, proximal shaft 14. The preferred method of attaching balloon necks 30, 32 to respective shafts 16, 14 is by thermal, or melt bonding, although suitable adhesive maybe used. The balloon of the invention is stretch blow-molded from a high-strength, bio-compatible, thermoplastic material, as is well known in the art of balloons for dilatation and/or stent delivery. In the preferred embodiment of the invention, the balloon is made of a thermoplastic elastomer, such as PEBAX®, a polyether block amide from Elf Atochem North America, Inc., Philadelphia, Pa.

Figure 3:
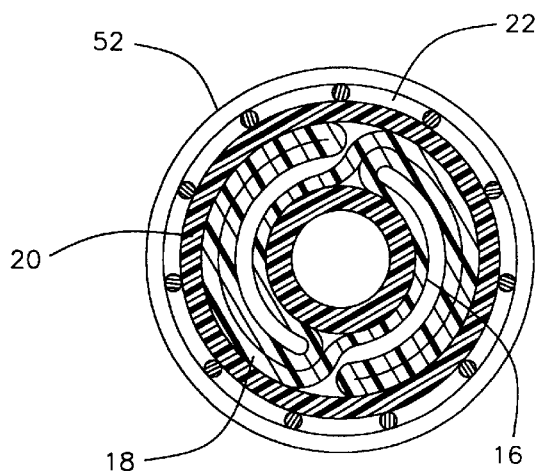
FIG. 3 is a transverse cross sectional view along lines 3—3 of FIG. 2.

Before sleeve 20 is mounted over balloon 18, the balloon is deflated, forming wings that are wrapped around distal shaft 16, as shown in FIG. 3. Sleeve 20 preferably extends beyond balloon 18 and is bonded directly to the catheter shaft, as shown adjacent proximal balloon neck 32 in FIG. 2. Alternatively, sleeve 20 may not extend beyond balloon 18, in which case sleeve 20 is bonded to balloon necks, as shown on distal balloon neck 30 in FIG. 2. Preferably, sleeve 20 is fastened to the respective points of attachment by thermal, or melt, bonding, although suitable adhesive may be used. For bonding purposes, proximal shaft 14, distal shaft 16, balloon 18 and sleeve 20 are all preferably made of melt compatible materials. Sleeve 20 is preferably made of a low durometer (Shore 40A–Shore 50A) thermoplastic polyurethane, such as Tecoflex™ by Thermo-Electron, Inc., Waltham, Mass. Alternative materials for sleeve 20 are low durometer grades of PEBAX®, such as 2533 or 3533. Stent 22 is crimped onto sleeve 20, and thus over balloon 18.

In the preferred embodiment of the invention, sleeve 20 should be longer than balloon 18 to an extent that, after sleeve 20 is bonded in position over balloon 18, excess, or slack sleeve material develops. To generate such excess material, the mounted length of sleeve 20 is shorter than the premounted length of sleeve 20. This slack material from sleeve 20 can then be used to retain stent 22 around balloon 18. Although the excess material can be formed in any portion of sleeve 20, it is preferred to induce the excess in proximal and distal portions of sleeve 20, where it will be gathered and folded to cover the ends of stent 22. Alternatively, sleeve 20 can be mounted about balloon 18 such that no slack, or excess material is formed thereby. In this alternative embodiment, sleeve material can be gathered, or drawn into one or more circumferential folds by longitudinally pulling, or stretching elastomeric sleeve material from either side of the fold being formed.

As shown in FIG. 2, the excess material of sleeve 20 is gathered and formed into proximal fold 50 and distal fold 52, which are formed at respective proximal and distal ends 54, 56 of stent 22. Once formed, proximal fold 50 is pulled in the distal direction and folded over stent proximal end 54. Similarly, distal fold 52 is pulled in the proximal direction and folded over stent distal end 56. After drawing folds 50, 52 over stent ends 54, 56 respectively, conventional heat shrink tubing is preferably used to heat treat folds 50, 52, setting a compressed shape therein. Optionally, the heat set process can partially embed folds into stent ends as shown by example in fold 50 and stent proximal end 54 in FIG. 2. In addition to establishing an engagement between folds 50, 52 and stent 22, the heat set process also reduces the overall profile of catheter 10 at stent 22.

The heat shrink tubing used is selected to be effective at temperatures that will heat set the material of sleeve 20 without altering the physical properties of biaxially oriented balloon 18. Suitable shrink tubing can be made of standard or irradiated polyethylene tubing that has been thermally expanded into a capture tube, then cooled. Alternatively, a variety of pre-expanded polyolefin shrink tubing is available from sources such as Raychem Corp., Menlo Park, Calif. After placing a length of selected shrink tubing over the distal end of the assembly comprising catheter 10, the application of hot air at the appropriate temperature causes the tubing to radially compress the assembly while conducted heat thermally sets the material of sleeve 20. During this heat setting step, the lumen of distal shaft 16 is preferably supported by a stainless steel wire mandrel.

Figure 7:
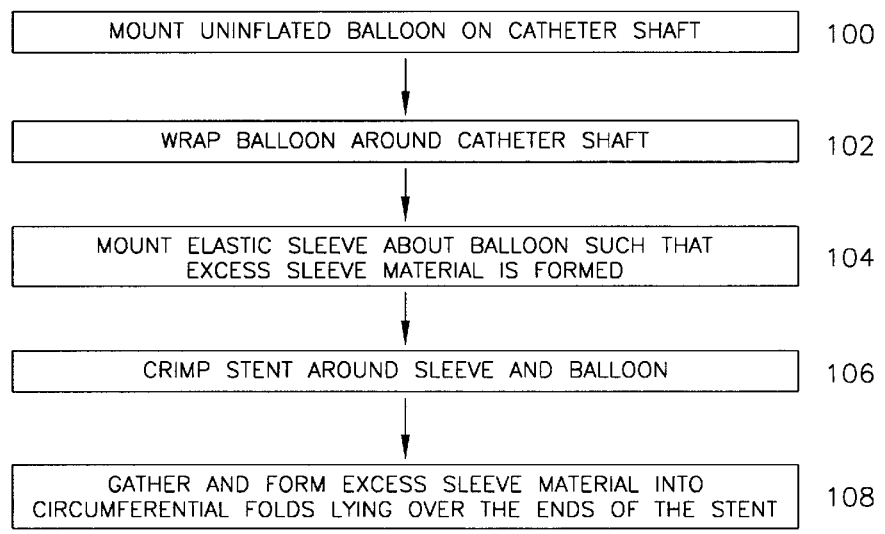
FIG. 7 is a flow chart depicting a method of making the stent delivery catheter of the present invention.

Similar to the flow chart shown in FIG. 7, the assembly steps for the invention preferably include:

(step 100) providing a tubular balloon having proximal and distal ends and mounting the balloon adjacent to and about the distal end of the catheter shaft and in fluid communication with the inflation lumen;

(step 102) wrapping the balloon around the catheter shaft;

(step 104) providing a sleeve formed of an elastic material, and having proximal and distal ends, and mounting the sleeve snugly about the balloon with the sleeve ends fixed to the balloon ends or to the shaft adjacent the balloon ends;

(step 106) providing a tubular stent having open ends and a stent length that is shorter than the length of the balloon, and crimping the stent about the sleeve and the balloon; and (step 108) gathering and forming the sleeve material into at least one circumferential fold that lies over at least one end of the stent.

Figure 4:
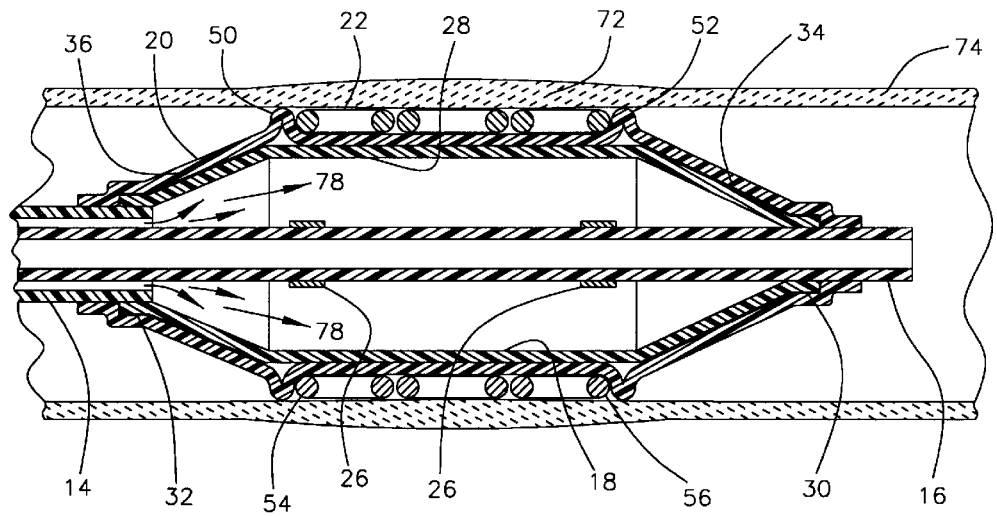
FIG. 4 is a longitudinal cross sectional view of the catheter with the stent partially expanded in a vessel narrowing.

In the operation of delivery catheter 10 of the present invention, and referring now to FIG. 4, catheter 10 is advanced to stenosis 72 in blood vessel 74. Once balloon 18 is placed within stenosis 72, as determined by one or more radiopaque marker bands 26 inside balloon 18, an inflation device (not shown) forces dilute radiopaque contrast media through an inflation lumen in proximal shaft 14 into the interior of balloon 18, as indicated by arrows 78. During expansion of balloon 18, sleeve 20 expands and stretches longitudinally, causing proximal and distal folds 50, 52 to unfold and pull off of stent 22. Expansion of balloon 18 and sleeve 20 also force stent 22 to expand against stenosis 72. FIG. 4 depicts partial deployment of stent 22, wherein folds 50, 52 have unfolded sufficiently to be pulled off of stent ends 54, 56 respectively. Full stent deployment may or may not completely unfold folds 50,52 and cause them to lie substantially flat against balloon cones 36, 34, depending on the amount of excess sleeve material that was gathered to create folds 50, 52.

Figure 5:
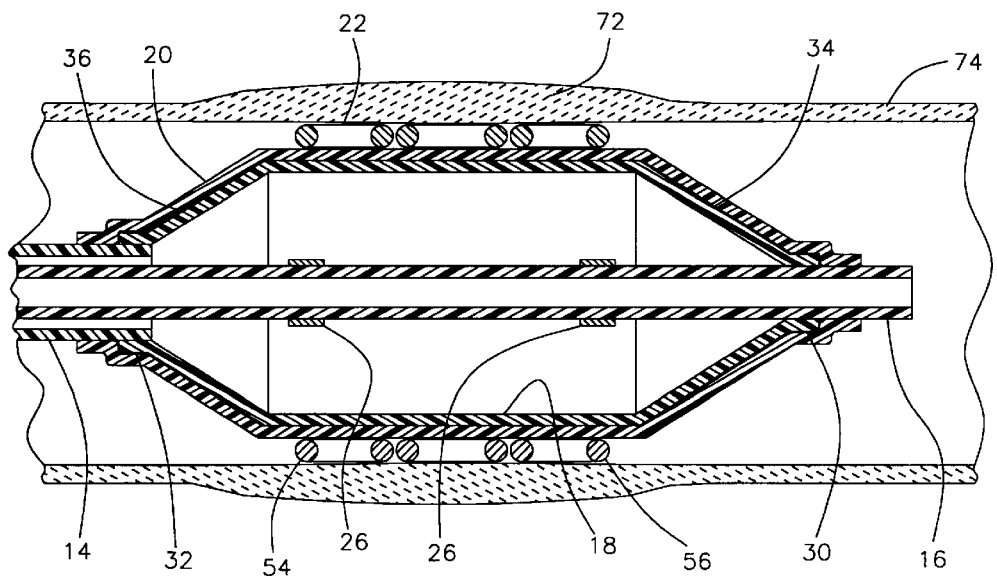
FIG. 5 is a longitudinal cross sectional view of the catheter with the stent fully expanded against the vessel narrowing.

FIG. 5. shows balloon 18 in a fully inflated state. With the concomitant expansion of sleeve 20, proximal fold 50 and distal fold 52 are depicted as having fully unfolded off of stent 22 and lie substantially flat against balloon 18. Stent 22 is fully expanded and has been deployed against dilated blood vessel 74. Following deployment of stent 22, catheter 10 is ready to be deflated to facilitate removal from the patient.

Figure 6:
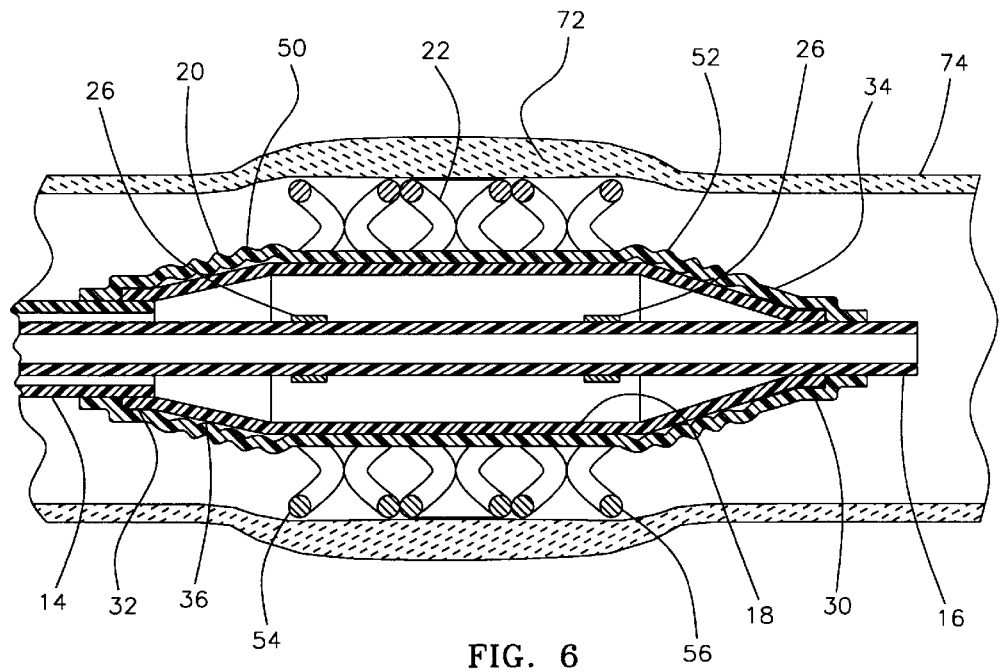
FIG. 6 is a longitudinal cross sectional view of the catheter with the stent deployed, and with the balloon partially deflated for withdrawal of the catheter from the blood vessel.

FIG. 6 shows balloon 18, which has been partially deflated by withdrawing inflation media through the inflation lumen in proximal shaft 14 to contract and separate the balloon from expanded stent 22. As balloon 18 contracts, elastomeric sleeve 20 also contracts and hugs balloon 18 as balloon 18 returns to substantially its original deflated condition. As shown in FIG. 6, folds 50 and 52 may begin to reappear as sleeve 20 is restored to its pre-deployment configuration. The elastomeric qualities of sleeve 20 enhance the ability of assembled catheter 10 to disengage from deployed stent 22 by reducing the balloon profile. Once separated from stent 22, delivery catheter 10 is then withdrawn from the patient's vascular system. Expanded stent 22 remains permanently deployed against blood vessel 74. It is to be understood that the particular stent delivery balloon catheter and method for manufacturing thereof are merely illustrative of the presently preferred embodiments of the invention and that no limitations are intended to the details of construction or design herein shown other than as described in the appended claims.

What is claimed is:

1. A stent delivery catheter comprising:

a catheter shaft having proximal and distal ends and an inflation lumen therein;

a tubular balloon having proximal and distal ends, the balloon being mounted on and wrapped around the catheter shaft adjacent the distal end thereof and in communication with the inflation lumen;

an elastic tubular sleeve having proximal and distal ends and a premounted length, the sleeve being mounted snugly around the balloon with a sleeve mounted length that is shorter than the premounted length such that excess sleeve material develops during the mounting of the sleeve on the catheter, the sleeve proximal and distal ends being fixed to the catheter shaft adjacent the proximal and distal ends of the balloon respectively;

an expandable stent having first and second ends and being shorter in length than the balloon, the stent being crimped about the sleeve and the balloon; and wherein the excess sleeve material is gathered and formed into a first circumferential fold lying over the first end of the stent.

2. The catheter of claim 1 wherein the excess sleeve material is further gathered and formed into a second circumferential fold lying over the second end of the stent.

3. The catheter of claim 1 wherein the first fold is partially embedded into the stent.

4. The catheter of claim 1 wherein the balloon is inflatable from a first configuration wherein the first fold lies over the first end of the stent, to a second configuration wherein the balloon and the stent are expanded for deployment of the stent in a vessel of a patient and wherein the first fold is unfolded sufficiently to uncover the first end of the stent.

5. The catheter of claim 4 wherein the balloon is deflatable from the second configuration to a third configuration wherein the balloon is substantially collapsed around the shaft and the sleeve lies compactly about the balloon such that the balloon and the sleeve are separated from the expanded stent to allow removal of the catheter from the vessel while the expanded stent remains deployed in the vessel.

6. The catheter of claim 1 wherein the elastic sleeve is formed of a thermoplastic elastomer.

7. The catheter of claim 6 wherein the thermoplastic elastomer is selected from materials comprising polyether block amide or polyether-based thermoplastic polyurethane.

8. A stent delivery system for a medical catheter, the system comprising:

an elongate, relatively inelastic balloon having a central axis and proximal and distal ends, the balloon being uninflated and furled about the axis;

an expandable tubular stent being mounted around the balloon, the stent having first and second ends and being shorter than the balloon; and an elastic tubular retainer being mounted between the stent and the balloon and extending beyond the ends of the stent, the retainer having formed therein a first circumferential fold that lies over the first end of the stent to hold the stent against the balloon.

9. The stent delivery system of claim 8 wherein the first circumferential fold is partially embedded into the stent.

10. The stent delivery system of claim 8 wherein the tubular retainer further has formed therein a second circumferential fold that lies over the second end of the stent to hold the stent against the balloon.

11. The stent delivery system of claim 8 wherein the retainer comprises a single layer of an elastomeric material, and the first circumferential fold comprises two layers of the material.

12. The stent delivery system of claim 11 wherein said elastomeric material is a synthetic rubber having a low durometer ranging from about Shore 40A to about Shore 50A.

13. A method of making a stent delivery catheter, comprising the steps of:
 (a) providing an elongate catheter shaft having proximal and distal ends and an inflation lumen;
 (b) providing a tubular balloon having proximal and distal ends and mounting the balloon adjacent to and about the distal end of the catheter shaft and in fluid communication with the inflation lumen;
 (c) wrapping the balloon around the catheter shaft;
 (d) providing a sleeve comprising an elastic material, and having proximal and distal ends and a premounted length, and mounting the sleeve snugly about the balloon with the sleeve ends fixed to the shaft adjacent the balloon ends;
 (e) providing a tubular stent having open ends and a stent length that is shorter than the balloon, and crimping the stent about the sleeve and the balloon; and
 (f) gathering and forming the sleeve material into at least one circumferential fold that lies over at least one end of the stent.

14. The method of claim 13 further comprising the step of heat setting and compressing the at least one circumferential fold to form a shape in the at least one fold.

15. The method of claim 14 wherein the step of heat setting and compressing the fold further embeds the fold at least partially into the stent.

* * * * *